United States Patent
Fukushima et al.

(10) Patent No.: US 10,166,313 B2
(45) Date of Patent: Jan. 1, 2019

(54) MEDICAL OR DENTAL MATERIAL FOR OSTEOGENESIS

(71) Applicants: Tadao Fukushima, Fukuoka (JP); Jun Yamazaki, Fukuoka (JP); Jun Ohno, Fukuoka (JP); Masako Toda, Fukuoka (JP); Makoto Mitarai, Ibaraki (JP); Keishi Iohara, Ibaraki (JP)

(72) Inventors: Tadao Fukushima, Fukuoka (JP); Jun Yamazaki, Fukuoka (JP); Jun Ohno, Fukuoka (JP); Masako Toda, Fukuoka (JP); Makoto Mitarai, Ibaraki (JP); Keishi Iohara, Ibaraki (JP)

(73) Assignee: MARUHA NICHIRO CORPORATION, Tokyo (JP)

( * ) Notice: Subject to any disclaimer, the term of this patent is extended or adjusted under 35 U.S.C. 154(b) by 272 days.

(21) Appl. No.: 15/024,520

(22) PCT Filed: Sep. 25, 2013

(86) PCT No.: PCT/JP2013/075953
§ 371 (c)(1),
(2) Date: Mar. 24, 2016

(87) PCT Pub. No.: WO2015/045044
PCT Pub. Date: Apr. 2, 2015

(65) Prior Publication Data
US 2016/0235888 A1    Aug. 18, 2016

(51) Int. Cl.
*A61K 6/00* (2006.01)
*A61L 27/26* (2006.01)
(Continued)

(52) U.S. Cl.
CPC ............ *A61L 27/26* (2013.01); *A61K 6/0082* (2013.01); *A61K 6/08* (2013.01); *A61K 6/097* (2013.01);
(Continued)

(58) Field of Classification Search
CPC ... A61K 6/0047; A61K 38/012; A61K 31/713
See application file for complete search history.

(56) References Cited

U.S. PATENT DOCUMENTS

2011/0257094 A1* 10/2011 Fukushima ............ A61K 6/033
514/8.8

FOREIGN PATENT DOCUMENTS

| JP | H08-239398 A | 9/1996 |
|----|--------------|--------|
| JP | H11-228526 A | 8/1999 |

(Continued)

OTHER PUBLICATIONS

He et al., "Characterization of peptide fragments from lung elastin degradation in chronic obstructive pulmonary disease," Exp Lung Res 36(9):548/557, 2010.*

(Continued)

*Primary Examiner* — Rosanne Kosson
(74) *Attorney, Agent, or Firm* — Foley & Lardner LLP (57) ABSTRACT

A bone-repairing agent excellent in workability and applicability to clinical surgical techniques and having a drastically enhanced bone formation rate, obtained by including an elastin hydrolysate in a complex of DNA and at least one selected from the group consisting of protamine, a protamine derivative, and a protamine hydrolysate can be provided. A medical or dental material for bone formation using this bone-repairing agent can be provided.

9 Claims, 5 Drawing Sheets

(51) Int. Cl.
*A61L 27/12* (2006.01)
*A61L 27/54* (2006.01)
*A61K 6/08* (2006.01)
*A61K 6/097* (2006.01)

(52) U.S. Cl.
CPC ............... *A61L 27/12* (2013.01); *A61L 27/54* (2013.01); *A61L 2300/252* (2013.01); *A61L 2300/258* (2013.01); *A61L 2300/414* (2013.01); *A61L 2400/06* (2013.01); *A61L 2430/02* (2013.01); *A61L 2430/12* (2013.01)

(56) References Cited

FOREIGN PATENT DOCUMENTS

| | | |
|---|---|---|
| JP | 2001-089436 A | 4/2001 |
| JP | 2001-327591 A | 11/2001 |
| JP | 4674288 B1 | 10/2005 |
| JP | 4354445 B2 | 4/2007 |
| JP | 2007-169201 A | 7/2007 |
| JP | 4718416 B1 | 5/2008 |
| JP | 4520477 B1 | 6/2008 |
| JP | 4801193 B1 | 7/2010 |
| JP | 2013-006799 A | 1/2013 |
| WO | WO-2010/110067 A1 | 9/2010 |

OTHER PUBLICATIONS

Toda, M. et al. "Protamine complex-induced bone regeneration by elastins or elastin peptide". The Journal of the Japanese Society for Dental Materials and Devices, Apr. 2013, vol. 32 No. 2, p. 83.

Kotani, M. et al. "Inhibitory effects of protamines on proteolytic and adhesive activities of Porphyromoras gingivalis." Infection and Immunity, Sep. 1999, vol. 67 No. 9, pp. 4917-4920.

Simionescu, A. et al. "Elastin-derived peptides and TGF-beta1 induce osteogenic responses in smooth muscle cells." Biochemical and Biophysical Research Communications, 2005, vol. 334, pp. 524-532.

Simionescu, A. et al. "Osteogenic Responses in Fibroblasts Activated by Elastin Degradation Products and Transforming Growth Factor-beta1". The American Journal of Pathology, Jul. 2007, vol. 171 No. 1, pp. 116-123.

\* cited by examiner

Water soluble elastin 20 %   Water soluble elastin 50 %

| | Enzymatic degradation product of elastin 20% | | Enzymatic degradation product of elastin 50% |
|---|---|---|---|
| (a-1) |  | (b-1) |  |
| (a-2) |  | (b-2) |  |
| (a-3) |  | (b-3) |  |
| | (a) | | (b) |

MEDICAL OR DENTAL MATERIAL FOR OSTEOGENESIS

CROSS-REFERENCE TO RELATED APPLICATIONS

This application is a national stage entry of International Application No. PCT/JP2013/075953, filed Sep. 25, 2013. The disclosure of this prior application is incorporated by reference herein in its entirety.

TECHNICAL FIELD

The present invention relates to a novel medical or dental material for osteogenesis, which is superior in bone formation rate and processability in comparison with a conventional material for osteogenesis, and which is obtained by adding an enzymatic decomposition product of elastin (molecular weight: 350 to 3,600 Da) into a DNA/protamine complex.

BACKGROUND ART

The number of patients of pyorrhea (periodontal disease) and osteoporosis increase with aging. Loss of teeth or malfunction of an artificial tooth occurs by loss of the jawbone (alveolar bone) and, when the diseases advance, any implant treatments become impossible. In such situation, surgery for recovering the jawbone is conducted. Although the most effective is transplantation of autologous bone in a site of bone loss, invasion for bone collection is high risk for elderly persons and sick persons. As an alternative material, an artificial bone such as hydroxyapatite is provided. However, such artificial bone has the problems common to the inorganic materials and has a drawback in terms of formability. Although many artificial bones are currently provided in the form of granules; when the morphology of the bone defect part have no complete recess form, the risk of outflow of the granules increases. In particular for elderly persons and sick persons having low-ered resistance, the outflow of the artificial bones having high fluidity with blood or external force has a risk of an important influence to the treatment process. Thus, the present inventors developed a DNA/protamine complex as a bone-repairing material excellent in workability, which is difficult to flow and yet capable of being directly injected through a syringe and easily moldable into a free shape (Patent Literature 1).

A protamine as a basic protein obtained from the testes (milt) of fish is reported to have an activity of inhibiting Arg-gingipain as a protease produced by *Porphyromonas gingivalis* (see Non Patent Literature 1). In addition, it is disclosed that periodontitis caused by a periodontal pathogen can be suppressed by further adding a protamine or a derivative thereof, and tranexamic acid and/or epsilon aminocaproic acid (see Patent Literature 2). These protamines are commonly used as a food preservative and are highly safe; thus, protamine is a promising medicine as an alternative to the conventional antimicrobial agents and antibiotics. Further, it is disclosed that protamine has a suppressing effect on growth of *Streptococcus mutans*, which is a caries-causing bacterium (see Patent Literature 3) and a suppressing effect on the adhesion of oral bacteria (see Patent Literature 4).

The present inventors have found that a protamine hydrolysate exhibited an antifungal activity against fungi, such as the genus *Candida*, causing oral candidosis (see Patent Literature 5). In addition, the present inventors have found that a protamine also had an anti-bacterial activity against periodontal disease bacteria, such as *Porphyromonas gingivalis* and *Prevotella intermedia* (see Patent Literature 1).

Protamine is a kind of polycations, and it is known that it forms a water-insoluble complex by generating an electrostatic binding with an anionic high molecular compound.

DNA obtained from the fish testes in the same manner as protamine has many phosphate groups providing anionic binding factors in the DNA molecule. Since such DNA exhibits an electrostatic affinity to a cationic substance; the DNA can form an electrostatic reactant with the cationic substance. It is disclosed that, although DNA molecule is poor in formability in itself and has a difficulty in control of its diffusion velocity through in vivo metabolism due to its water-solubility, a water-insoluble and self-supporting transparent film can be prepared by electrostatically binding a DNA molecule to an artificial cationic lipid (see Patent Literature 6).

A film consisting of a complex of DNA and a lipid is also known. The DNA/lipid complex film, in which the DNA molecule as a biopolymer keeps a regular double helix structure, enables various low-molecular compounds to intercalate into the spaces between DNA bases in the double helix structure, and similar low-molecular compounds to groove-bind in the two grooves (main and minor grooves) of the DNA. A method of producing a medical material by intercalating and/or groove-binding a medicinal ingredient to the DNA/lipid complex film was invented (see Patent Literature 7).

The present inventors focused attention on the fact that chitosan already used as a medical and/or dental material was a cationic substance and, thus, the present inventors made an invention based on that a complex of a DNA molecule and chitosan held a double helix structure specific to DNA, insolubility in water, biocompatibility, antibacterial activity and a good formability (see Patent Literature 8). The present inventors also invented a method for easily molding a DNA/chitosan complex into a thread form, a ball form, or a disk form by suspending it in a phosphate buffer solution (see Patent Literature 9); and a method for producing a film by compression-molding such a complex under heating (see Patent Literature 10). The DNA/chitosan complex and its molded products have been a promising one as a medical and/or dental material, because it had an excellent biocompatibility and biostability.

There are the prior literatures relate to elastin, which is present in the elastic tissues of the body, such as the ligament, blood vessels, the heart, and the skin, and which activates transforming growth factor-β1 (TGF-β1) and induces bone formation reaction (see Non Patent Literatures 2 and 3). There are two type of elastin from Elastin Products Company, Inc., which were used in these prior literatures, i. e., α-elastin having a molecular weight of 6,600 to 47,000 Da, extracted from the nature, and an elastin peptide having a molecular weight of 1,000 to 25,000 Da, obtained by degradation by acid and/or alkali treatment. Alpha-Elastin from Elastin Products Company, Inc. can be obtained by dissolving a bovine neck ligament by a high temperature oxalic acid, separating and removing β-elastin by a coacervation method after purification and desalting. The acid- and/or alkali-treated elastin can be obtained by washing a bovine neck ligament with hot water to remove soluble contaminating proteins, boiling the resultant in an alkaline solution, and hydrolyzing and purifying the insoluble fraction. Both of these elastins are water soluble.

However, although the effect of elastin to induce bone formation by the in vitro investigation has been recognized, it is necessary that elastin has formability or that elastin is included in another material. Even if elastin is contained in a prior art material by impregnation, dissolution and outflow of elastin in vivo in a very short time has been expected. Therefore, elastin has not been considered to exhibit sufficient bone formation ability. The elastin can be cross-linked using a crosslinking agent, etc., to provide formability to elastin. However, it is desirable to minimize the use of an agent such as a crosslinking agent in a bone formation material because there is concern that the crosslinking agent itself causes a reaction against a foreign material or a toxic reaction in vivo.

PRIOR ART LITERATURE

Patent Literature

Patent Literature 1: Japanese Patent No. 4801193
Patent Literature 2: Japanese Patent Laid-Open No. 2007-169201
Patent Literature 3: Japanese Patent Laid-Open No. 228526/1999 (H11-228526)
Patent Literature 4: Japanese Patent Laid-Open No. 2001-89436
Patent Literature 5: Japanese Patent No. 4520477
Patent Literature 6: Japanese Patent Laid-Open No. 239398/1996 (H08-239398)
Patent Literature 7: Japanese Patent Laid-Open No. 2001-327591
Patent Literature 8: Japanese Patent No. 4674288
Patent Literature 9: Japanese Patent No. 4354445
Patent Literature 10: Japanese Patent No. 4718416

Non Patent Literature

Non Patent Literature 1:
Kotani M. and five others, "Inhibitory effects of protamines on proteolytic and adhesive activities of *Porphyromonas gingivalis*", Infection Immunity, 1999, Vol. 67, No. 9, p. 4917-4920
Non Patent Literature 2:
Agneta Simionescu, and three others, "Elastin-derived peptides and TGF-β1 induce osteogenic responses in smooth muscle cells", Biochemical and Biophysical Research Communications, 2005, Vol. 334, p. 524-532
Non Patent Literature 3:
Agneta Simionescu, and three others, "Osteogenic Responses in Fibroblasts Activated by Elastin Degradation Products and Transforming Growth Factor-β1", The American Journal of Pathology, 2007, Vol. 171, No. 1, p. 116-123

SUMMARY OF INVENTION

Technical Problems to be Solved by the Invention

As described above, it is the present situation that the artificial bones now used have a problem regarding fluidity, etc. and that there is no bone-repairing materials which are effective and versatile in elderly persons and sick persons. The DNA/chitosan complex of Patent Literature 8, the DNA/chitosan complex molded product of Patent Literature 9, and the DNA/chitosan complex film of Patent Literature 10 exhibited an acute inflammatory reaction in vivo and chitosan is difficult to be decomposed in vivo. Therefore, a material having higher biocompatibility and good biodegradability has been desirable. In addition, the DNA/protamine complex of Patent Literature 1 induces a very slight inflammatory reaction in vivo, which has not only an excellent biocompatibility, but also a formability enabling to easily mold it to a desired shape. Although the problem of the formability has been solved, it is further desired that the bone formation rate is higher and bone repair is achieved in a short period, in order to achieve efficient bone repair. In addition, although the osteogenesis-inducing effect was recognized in the in vitro investigation regarding the elastins of Non Patent Literatures 2 and 3, they have a problem in that they cannot maintain their shapes in vivo regarding their clinical application. Therefore, even if they are molded with an cross-linking agent, there is concern regarding a harmful influence of the residual cross-linking agent to a living body and, thus, elastin has not been a material usable as material for osteogenesis The present invention has been achieved regarding the above prior art techniques. An object of the present invention is to provide a material for osteogenesis consisting of a highly safety materials without using any chemicals such as a cross-linking agent, which has water-insolubility, a good formability to easily mold it to a desired shape, an excellent bone formation rate to achieve a rapid bone repair, without concern of side-effects.

Means for Solving the Problems

As a result of the earnest and repeated research for solving the above described problems, the present inventors have found that the ability of osteogenesis of an enzymatic degradation product of elastin is especially high by adjusting its molecular weight in the rage from 350 to 3,600 Da by protease treatment in order to increase the ability for osteogenesis of a naturally-derived elastin; and that not only the problems concerning the formability can be solved, but also the bone formation rate can be dramatically improved by combining the enzymatic degradation product of elastin with a DNA/protamine complex.

The medical or dental material for osteogenesis according to the present invention is characterized by comprising a complex comprising:
(1) DNA;
(2) at least one selected from the group consisting of protamine, a protamine derivative, and a protamine hydrolysate; and
(3) an enzymatic degradation product of elastin, as an active component for osteogenesis.

Effects of Invention

According to the present invention, not only a bone repair agent suitable for a clinical application with an excellent processability, but also a bone repair agent with a dramatic improvement of its bone formation rate, which has been not provided in the prior art techniques, can be provided by combining a DNA/protamine complex with an enzymatic degradation product of elastin obtained by hydrolysis treatment in order to increase the osteogenesis ability of elastin.

Among the complexes according to the present invention, the DNA/protamine complex can be used as a guided periodontal tissue regeneration (GTR) membrane, in a guided bone regeneration (GBR) method, as an antibacterial denture liniment, and further as an intraoral antibacterial agent, a hemostatic agent, one of various sanitary goods, etc., because it is excellent in biocompatibility and stability in vivo and further it has a formability to easily mold it to a desired shape. In addition, a bone formation material can be provided, whose bone formation rate is increased by carrying a growth factor (e.g., b-FGF or BMP) on DNA, because DNA enables intercalation or grove binding of a low-molecular compound. Furthermore, a medicine such as an antibiotic can be carried thereon to use the complex as a membrane, a film, a lining material, or a coating material for a delivery system (DDS), which is capable of delivering and supplying it to the necessary areas, such as an affected area, in need thereof. The complex can also be variously used not only as a dental material but also as a medical material, for example, as a scaffold material for regenerative medicine, as a wound dressing material, as an infection-preventing membrane, as an adhesion-preventing membrane, or as an implant material.

According to the clinical application of the present invention, a material for osteogenesis, which is excellent in its bone formation rate and processability against the material for osteogenesis of the prior art techniques and which is easily and conveniently treated at an clinical operation, can be provided to patients suffering periodontitis, bone fracture caused by tumbling of elderly persons, or complex fracture caused by accidents. The present technique is expected not only to contribute to the development of a state-of-the-art bone regenerative medicine technique, but also to contribute to aiding recovery from reduced motor function due to bone fracture, and to extension of the healthy life expectancy of the people.

BRIEF DESCRIPTION OF DRAWINGS

FIG. 4 The state of the µCT images of DNA/protamine complex-embedded areas (1 to 3 months after embedding) is shown, when 20% (w/w) of water-insoluble elastin was added in FIG. 4(a), and when 50% (w/w) water-insoluble elastin was added. in FIG. 4(b), respectively.

FIG. 5 The state of the µCT images of DNA/protamine complex-embedded areas (1 to 3 months after embedding) is shown, when 20% (w/w) of water-soluble elastin was added in FIG. 5(a), and when 50% (w/w) water-soluble elastin was added. in FIG. 5(b), respectively.

FIG. 6 The state of the µCT images of DNA/protamine complex-embedded areas (1 to 3 months after embedding) is shown, when 20% (w/w) of an enzymatic degradation product of elastin was added in FIG. 6(a), and when 50% (w/w) of an enzymatic degradation product of elastin was added in FIG. 6(b), respectively.

DETAILED DESCRIPTION OF INVENTION

Description of Embodiments

The present invention will now be described in detail.

DNA, both a DNA of a natural origin and a synthetic DNA, can be used. Examples of a DNA of a natural origin include a λ phage DNA of a bacterial virus, an *Escherichia coli* chromosome DNA, a calf thymus DNA, and a sperm DNA of fish, such as salmon, herring, and trout. Examples of a synthetic DNA include various synthetic DNAs having different nucleotide sequences obtained by synthesis in a synthesis device using poly(dA), poly(dT), poly(dG), poly (dC), poly(dA-dT), poly(dG-dC), etc; various synthetic RNAs having different nucleotide sequences obtained by synthesis in a synthesis device using poly(A), poly(T), poly(G), poly(U), poly(A-T), poly(G-U), etc.; and a DNA/RNA hybrid having complementary base pairs obtained by synthesis in a synthesis device using a DNA/RNA hybrid of poly(dG), poly(U), poly(G), poly(dC), poly(dA-dT), poly (A-T), etc. These DNAs may be used singly or in a combination of two or more than two of them according to need.

There is no particular restriction on the molecular weight of a DNA, insofar as a double helix structure is maintained to intended extent. With respect to the molecular weight of a DNA, a DNA with 10 bp to 30,000 bp can be used. In case the molecular weight is too high, the preparation of an aqueous solution becomes difficult; while, in case the molecular weight is too low, the recovery rate of a complex becomes low. Therefore, the use of a DNA having the center of the molecular weight distribution between 300 bp and 7,000 bp is preferable.

Such DNA has a structure having various groups, such as groups carrying a phosphoric acid-containing group at their terminals, which bind with the four kinds of the bases [cytosine (C), guanine (G), adenine (A), and thymine (T)] forming the double helix structure. Such DNA expresses anionic property, on the whole, due to, for example, the above phosphate groups, etc. bonded to terminals.

Such DNA itself has a string-like shape with a double helix structure. Since the DNA is soluble in water, the DNA itself is lacking formability. Taking advantage of the anionic property of the DNA, a DNA/protamine complex can be obtained by reacting electrostatically the anionic DNA and a cationic protamine. By forming such a complex, the DNA becomes practically insoluble in water. Further, the solubility in an organic solvent becomes also lower.

A protamine is a strongly basic protein existing as a nucleoprotamine bonded with a DNA in a sperm nucleus of fish, such as salmon, herring and trout, and referred to as salmine (from salmon), clupeine (from herring), etc. according to difference in their sources. They have slightly different structures, respectively, but any of the protamines can be utilized.

The term "a protamine derivative" refers to a salt of a protamine with an inorganic acid or an organic acid, or a salt with an inorganic base or an organic base. Depending on the intended use of the salt, an acid or a base may be selected, and in view of the uses such as foods, cosmetics, and pharmaceuticals, the following pharmaceutically acceptable salts are preferable. Namely, examples of an acid addition salt include a hydrochloride, a nitrate, a sulfate, a methanesulfonate, a p-toluenesulfonate, as well as a salt with a dicarboxylic acid, such as oxalic acid, malonic acid, succinic acid, maleic acid, and fumaric acid, and a salt with a monocarboxylic acid, such as acetic acid, propionic acid, and butyric acid. Examples of an inorganic base suitable for forming a salt of a peptide compound to be obtained according to the present invention include hydroxides, carbonates, and bicarbonate of ammonia, sodium, lithium, calcium, magnesium, and aluminum. Examples of a salt with an organic base include a salt of a mono-, di- or tri-alkylamine, such as methylamine, dimethylamine, and triethylamine; mono-, di- and tri-hydroxyalkylamine salts; a guanidine salt; and an N-methylglucosamine salt. These protamine derivatives can be used alone or in a combination of two or more than two of them according to need.

Hydrolysates of a protamine are prepared by hydrolyzing a protamine using an acid, an alkaline substance, a protease, or a combination thereof. Hydrolysis using a protease is preferable. A more detailed process of the hydrolysis is as follows. A solvent for the hydrolysis treatment such as deionized water is added to a protamine, and then the pH is adjusted to the optimum pH for an enzyme by adding sodium hydroxide or hydrochloric acid. After heated up to the optimum temperature for the enzyme, the enzyme is added and the enzymatic reaction is conducted with stirring. After the completion of the reaction, the reaction liquid is heated to 80° C. to 100° C. for 5 min to 60 min for deactivation by heat, the pH is adjusted to a neutral zone, and then the reaction liquid is freeze-dried to yield decomposition products of the protamine. These protamine degradation products can be used alone or in a combination of two or more than two of them according to need.

With respect to the decomposition products of a protamine prepared according to the above process, a completely decomposed protamine exhibits almost no antimicrobial activity. Consequently, it should preferably be partially decomposed, so that their molecular weights distribute in the range of 500 to 4,000 Da.

Examples of a protease usable for hydrolysis of a protamine include enzymes produced by bacteria belonging to genus *Bacillus*, such as *Bacillus subtilis*, *Bacillus thermoproteolyticus*, and *Bacillus licheniformis*; enzymes produced by molds belonging to genus *Aspergillus*, such as *Aspergillus oryzae*, *Aspergillus niger*, and *Aspergillus mellens*; and enzymes produced by molds belonging to genus *Rhizopus*, such as *Rhizopus niveus*, and *Rhizopus delemar*, as well as pepsin, pancreatin, and papain. The enzymes may be used singly or in combination of two or more enzymes. The protease is classified into an endopeptidase, which cleaves a protein through specific recognition site(s) of an internal sequence of the same, and an exopeptidase, which cleaves every 1 or 2 terminal amino acid residues. Therefore, according to need, various peptide chains can be yielded by a combination of an endopeptidase and an exopeptidase. In the case of hydrolysis by an enzyme, 0.001% to 10% of the enzyme is added with respect to a substrate, and the solution is adjusted to the optimum pH for the enzyme(s) to be used, and then hydrolyzed.

The protamine, protamine derivative, and protamine degradation product of the present invention have antimicrobial activity against Gram-positive bacteria, such as bacteria of the genus *Bacillus*, bacteria of the genus *Streptococcus*, and lactic bacteria, fungi such as fungi of the genus *Candida*, and periodontal disease bacteria, such as bacteria of the genus *Porphyromonas* and bacteria of the genus *Prevotella*.

The complex of DNA and protamine can be prepared by reacting protamine with at least one of protamine, protamine derivatives, and protamine hydrolysates in an aqueous medium. For example, an aqueous DNA solution is added to and mixed with an aqueous protamine solution under stirring so as to react them.

The mixing ratio of a DNA to at least one of a protamine, derivatives of a protamine and hydrolysates of a protamine can be selected according to an intended use of the complex. It can be selected within, for example, a range of 1/9 to 9/1, and preferably 1/1 to 1/1.5 (weight ratio).

The complex can be formed as precipitate by reacting a DNA with at least one of a protamine, derivatives of a protamine and hydrolysates of a protamine in an aqueous medium. The precipitate thus obtained is washed with water or various buffer solutions. The precipitate is further washed with water according to need. Excess water is then removed by centrifugation, etc. followed by drying, and a dry complex can be thus obtained. A process for drying may be appropriately selected and used according to an intended purpose from a normal temperature drying process, a heat-drying process, a freeze-drying process, and a reduced-pressure drying.

A buffer solution for washing a precipitate may be selected from a Tris buffer solution, a borate buffer solution, a HEPES buffer solution, an acetate buffer solution, a citrate buffer solution, a glycine buffer solution, a barbiturate buffer solution, a phthalate buffer solution, a cacodylate buffer solution, a carbonate buffer solution, a Bis-Tris buffer solution, a Bis-Tris propane buffer solution, an MES buffer solution, an ADA buffer solution, a PIPES buffer solution, an ACES buffer solution, a cholamine chloride buffer solution, a BES buffer solution, an MOPS buffer solution, a TES buffer solution, an HEPPS buffer solution, a Tricine buffer solution, a glycinamide buffer solution, a bicine buffer solution, a TAPS buffer solution, a CHES buffer solution, a CAPS buffer solution, a phosphate buffer solution, etc. The concentration and the pH of a buffer solution may be freely selected so as to obtain a DNA/protamine complex with the desired attributes and properties.

As the elastin used in the present invention, fish-derived, bovine-derived, or porcine-derived elastin may be used. Examples of the fish for preparing elastin can include fishes in the family Salmonidae of the order Salmoniformes, such as salmon and trout, fishes in the family Scombridae of the order Perciformes, such as tuna and bonito, fishes in the family Carangidae of the order Perciformes, such as yellowtail, and fishes in the family Hexagrammidae of the order Scorpaeniformes, such as ling cod.

An enzymatic degradation product of water-insoluble elastin is used in order to cause elastin to exhibit an excellent ability for osteogenesis by adding elastin to a DNA/protamine complex. The water-insoluble elastin is obtained by using the heart cardiac bulbus arteriosus of fish, a cow, or a pig as a raw material, stirring the bulbus arteriosus in a 0.01 to 0.1% (w/v) sodium hydroxide aqueous solution at 10 to 60° C. for 2 hours to 48 hours to dissolve contaminating proteins, followed by washing with water or neutralization with hydrochloric acid. However, since there is possibility that elastin dissolves under a too high alkali concentration, stirring is preferably performed in a 0.04 to 0.06% sodium hydroxide aqueous solution at 30 to 45° C. for 12 to 18 hours. Heating at 70° C. or higher for 5 minutes or more after neutralization is preferable in order to dissolve and remove soluble contaminating substances. The range of the molecular weight of water-soluble elastin used in the present invention for enzymatic decomposition is from about 9,100 Da to about 97,500 Da. Regarding the kind of the enzyme for enzymatic decomposition, any proteases acting under a neutral or an alkaline condition can be used. Proteases derived from bacteria of the genus *Bacillus* are suitable. Enzymatic decomposition products can be efficiently obtained preferably by using two or more proteases derived from bacteria of the genus *Bacillus*. A concrete example includes a combination of Alcalase 2.4 L FG (Novozymes A/S) and Protex 6 L (Genencor Kyowa Co. Ltd.). The conditions for the enzymatic reactions may include pH from 6 to 12, temperature of 40 to 70° C., reaction time from 30 minutes to 24 hours, and a concentration of the enzyme to be added from 0.1 to 2.0% based on the dry weight of a substrate. Enzymatic decomposition products can be efficiently obtained preferably by carrying out the enzymatic reaction under the conditions of a pH of 6 to 9, at 60° C., for 2 to 6 hours. As the molecular weight distributions of the enzymatic decomposition products, molecular weights of the enzymatic decomposition products distribute preferably in the range of from 350 and 3600 Da and the molecular weight distribution preferably include at least the range from 350 to 990 Da.

The mixing ratio of an enzymatic degradation product of elastin in the DNA/protamine complex can be set so that the desired osteogenesis ability is obtained. For example, the mixing ratio of the enzymatic degradation product of elastin in the DNA/protamine complex can be selected from the range of 1 to 75% (w/w), preferably the range of 20 to 50% (w/w), more preferably 50%. In other words, the enzymatic degradation product of elastin can be blended in an amount of 1 to 75 parts by weight, preferably 20 to 50 parts by weight, more preferably 50 parts by weight, based on 100 parts by weight of the DNA/protamine complex (solid content).

An easily moldable state can be obtained by adding an appropriate amount of water to a dried product of the complex of DNA and protamine and kneading in a mortar to make the mixture to obtain the easily moldable state such as a paste form, a gel form, or a sticky paste depending on the kneading time. A DNA/protamine/elastin complex can be obtained by simultaneously kneading the mixture, while an enzymatic degradation product of elastin is added. In the DNA/protamine/elastin complex, DNA binds to at least one of protamines, protamine derivatives and hydrolysates of protamine to make complex matrixes and the DNA/protamine/elastin complex comprises a structure in which the enzymatic degradation product of elastin are incorporated in the complex matrixes. The enzymatic degradation product is held in the complex matrixes without release, when it is placed to the site to be treated by incorporating the enzymatic degradation product of elastin in the complex matrixes. As a result, the enzymatic degradation product exhibits the effect to further enhance the osteogenesis ability of the DNA/protamine complex at the site to be treated.

The kneaded product of the DNA/protamine/elastin complex has high stickiness and resilience (flexibility) and, thus, has a formability for easily molding into a desired shape, such as a string shape, a belt shape, or a mountain shape, when applied to a site to be treated and enabling stable maintenance at least during application to the site to be treated without the divergence of its shape.

In addition, each of the pastes of these complexes is extruded into a phosphate buffer solution using a syringe to provide a string-shaped molded product. A mold according to the purpose can be filled by the paste to provide any of molded products of various shapes, such as a rod shape, a spherical shape, and a disk shape.

Each of the film-shaped molded products of these complexes can be obtained by pressing a dry powder of the complex, or its formed product in a paste form, a rod form, a spherical form or a disk form by using a heated forming machine. Further, a transparent film can be easily formed by extending thinly the formed product of a protamine/DNA/elastin complex in a mortar.

The temperature during the formation of a film using the heated forming machine can be set variously depending on a material for forming a film. The temperature can preferably be selected within a range between room temperature (e.g. 15° C. to 25° C.) and 120° C. The pressing pressure during the film formation can be selected within a range between 2 MPa and 20 MPa. The pressing time duration is selected so as to obtain required properties of the film. When the above temperature and pressing pressure are used, the film formation can be completed, for example, within 1 min to 10 min. Preferably by pressing for 5 min to 10 min a tough and unbreakable film can be formed. The film thickness can be regulated by the temperature, the pressure, and the pressing time duration during pressing. A transparent complex film with a film thickness of about 1 μm to 100 μm can be obtained according to the above process.

The material for osteogenesis according to the present invention can be used as a guided tissue regeneration (GTR) membrane in a GTR method of regenerating lost periodontal tissue. Especially, a dental material containing the DNA/protamine/elastin complex is excellent in biocompatibility (adaptability) and is particularly preferable as a structural component of the GTR membrane. The GTR membrane is a material to form an environment for regeneration of the alveolar bone, the periodontal membrane, the cementum, etc., by shielding them from the epithelial tissue antecedently growing in a lost site. The membrane is preferably formed of a highly biocompatible material, because it is anchored in the body for a certain period of time, and further preferably has antimicrobial properties against periodontal disease bacteria etc. As such membranes, an absorbable membrane having collagen or polylactic acid as a substrate, and a non-absorbable membrane using a fluorocarbon resin have been used. A GTR membrane consisting of a film-, gel-, or paste-shaped product of the DNA/protamine/elastin complex according to the present invention has high biocompatibility and can be stably used for a longer period of time than conventional such membranes. The regeneration period can be set longer than the uses of the conventional absorbable membranes, by using a GTR membrane produced using a dental material according to the present invention.

In the DNA/protamine/elastin complex, although the electrostatic binding of some of the phosphate groups of DNA as anionic groups to cationic groups of protamine results in the exertion of the desired shape-forming properties, many phosphate groups, which are not binding to protamine, remain in the DNA molecule. Such phosphate groups can be advantageously used for electrostatic bonding of a bone morphogenetic factor or a growth factor and used also as a carrier of these cytokines or antibiotics. In addition, the complex can be a carrier of a medicine through intercalation or groove binding of the double helix structure of the DNA.

The bone formation factor and the growth factor can be utilized without particular limitation provided that they can be carried on a DNA/protamine/elastin complex. Examples of the bone morphogenetic factors include bone morphogenetic protein (BMP), and recombinant human bone morphogenetic protein (rhBMP). Examples of the growth factors include fibroblast growth factor (FGF), transforming growth factor beta (TGF-β), epidermal growth factor (EGF), insulin-like growth factor (IGF), platelet-derived growth factor (PDGF), vascular cell growth factor (VEGF), and neurotrophic factor (NGF). At least one of the above substances can be used.

A DNA/protamine/elastin complex can be mixed with powdery or granular calcium phosphate by kneading or otherwise to obtain a mixture having formability. During the preparation of the mixture, an appropriate amount of water or a phosphate buffer solution may be added according to need to obtain a paste with formability. Calcium phosphate in a form of granule or powder becomes formable through the formation of the mixture. More particularly, a kneaded mixture of the DNA/protamine/elastin complex and calcium phosphate in a form of granule or powder can be formed into any form by packing the mixture into a mold, or packed in a bone defective part with a complicated shape by injection from a syringe filled with the mixture. Further, after a mixture paste is formed into a desired shape, the shaped paste can be subjected to a drying treatment to fix the desired shape of the mixture. The mixture can be used for applications as a regeneration inducting agent or a regeneration promoting agent for a paradentium (specifically, alveolar bone, periodontal ligament, and cementum) in a paradentium regeneration therapy, or as a bone filling material for inducing or promoting osteogenesis at a bone defective part. However, the applications of the mixture are not limited.

Examples of the calcium phosphate materials include hydroxyapatite (HA), tricalcium phosphate (α-TCP, β-TCP), calcium hydrogen phosphate dihydrate (DCPD), octacalcium phosphate (OCP), tetracalcium phosphate (TeCP), and carbonate apatite (CAP). At least one of these materials can be used.

The DNA/protamine/elastin complex can be formed not only as the above described dental material, but also as a film, a lining material or a coating material, which can be used as a scaffold material for regenerative medicine, a wound dressing, an infection prevention membrane, and an adhesion prevention membrane. Thus, the complex can be used as a medical material characterized by improving the bio-compatibility on the occasion of transplantation, or suppressing the biological reaction to a xenobiotic.

EXAMPLES

A best mode for carrying out the present invention will now be described in detail with reference to Examples. However, the present invention is not limited to the following Examples.

Example 1

(Preparation of DNA/Protamine Complex)

An aqueous solution of a protamine sulfate originated from milt of chum salmon (Proserve; by Maruha Nichiro Foods, Inc.) at a concentration of 57% (w/v), and an aqueous solution of a DNA also originated from milt of chum salmon (the center of the molecular weight distribution of 300 bp; by Maruha Nichiro Foods, Inc.) at a concentration of 0.5% (w/v) were used. In order to make the respective weights of the protamine sulfate and the DNA to 1:1, 0.875 g of the aqueous solution of a protamine sulfate was diluted by 100 mL of sterile distilled water and mixed with 100 mL of the DNA solution, and stirred for 1 hour. Precipitate was recovered by centrifugation, washed with water, and centrifuged again to recover the precipitate thus washed as a DNA/protamine complex (undried). The DNA/protamine complex (undried) was further freeze-dried to yield 0.61 g of a DNA/protamine complex. The recovery rate of the DNA/protamine complex was 61 weight % (w/w).

(Preparation of Elastin)

Figure 1:
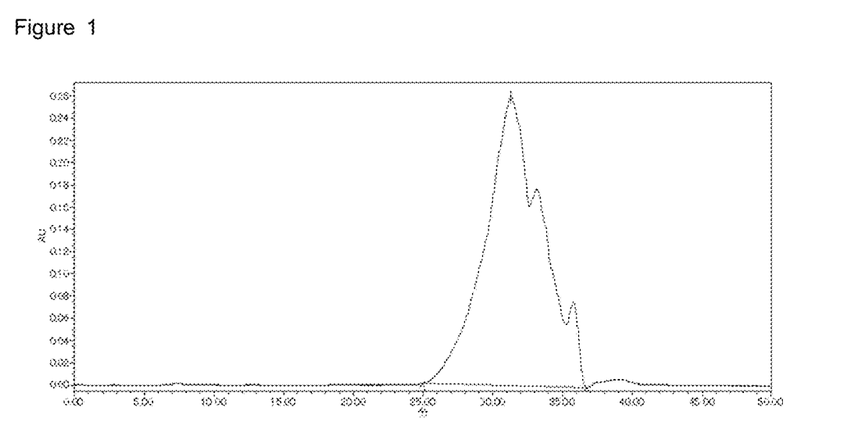
FIG. 1 is a chromatogram when water-soluble elastin was analyzed by gel filtration chromatography.
Figure 2:
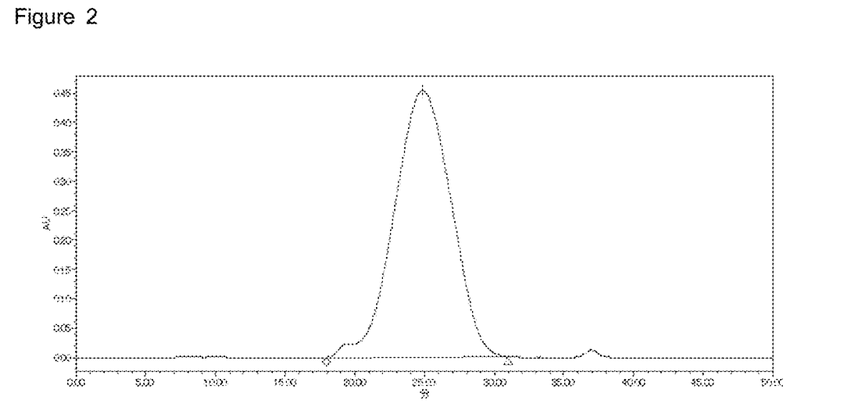
FIG. 2 is a chromatogram when water-soluble elastin was analyzed by gel filtration chromatography.
Figure 3:
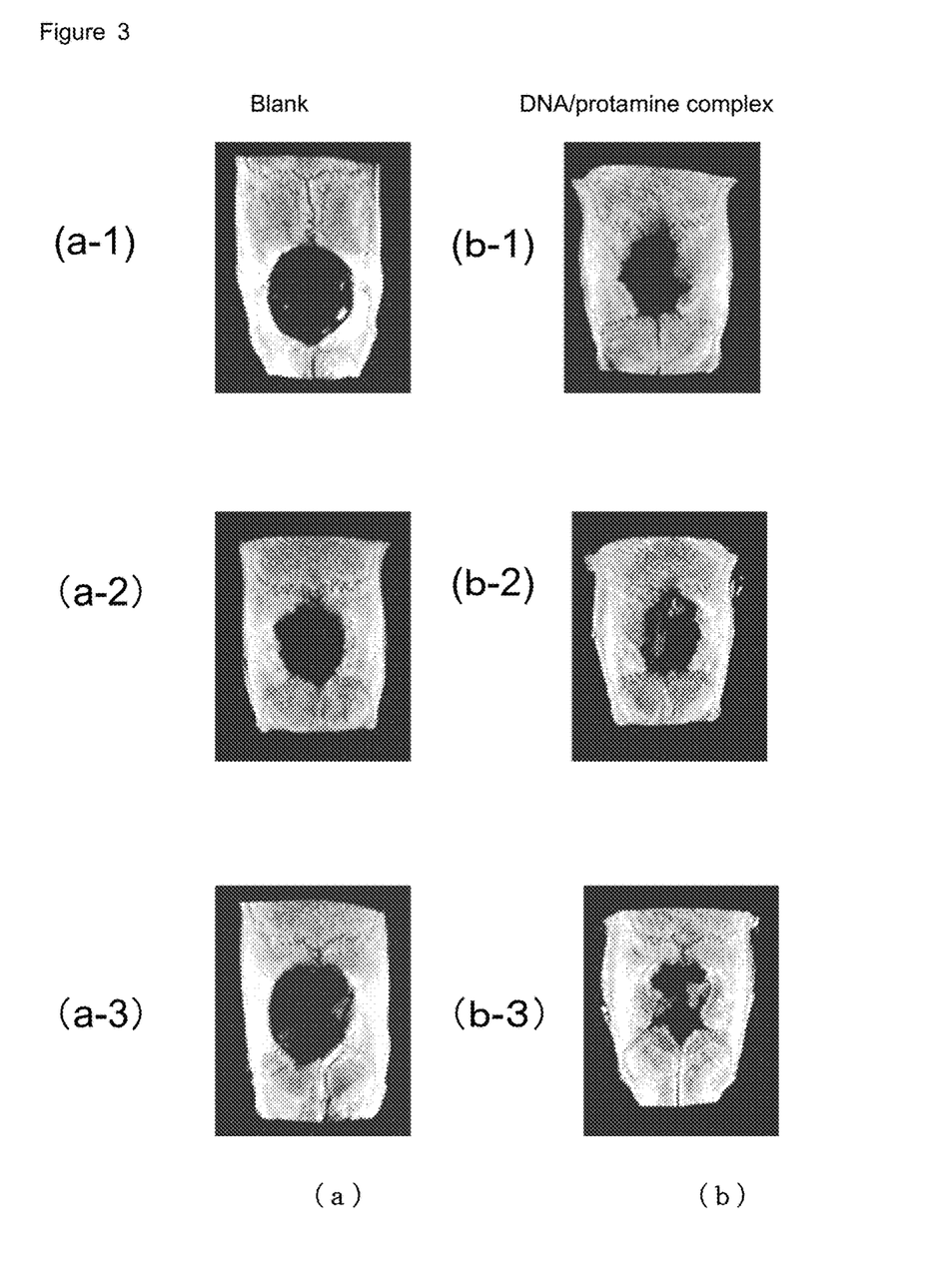
FIG. 3(a) shows the state of the µCT images (1 to 3 months after embedding), when no material was embedded in the bone defect part and the part was sutured.
FIG. 3(b) shows the state of the µCT images of a DNA/protamine complex embedded part (1 to 3 months after embedding), when the DNA/protamine complex alone was embedded, respectively.
Figure 4:
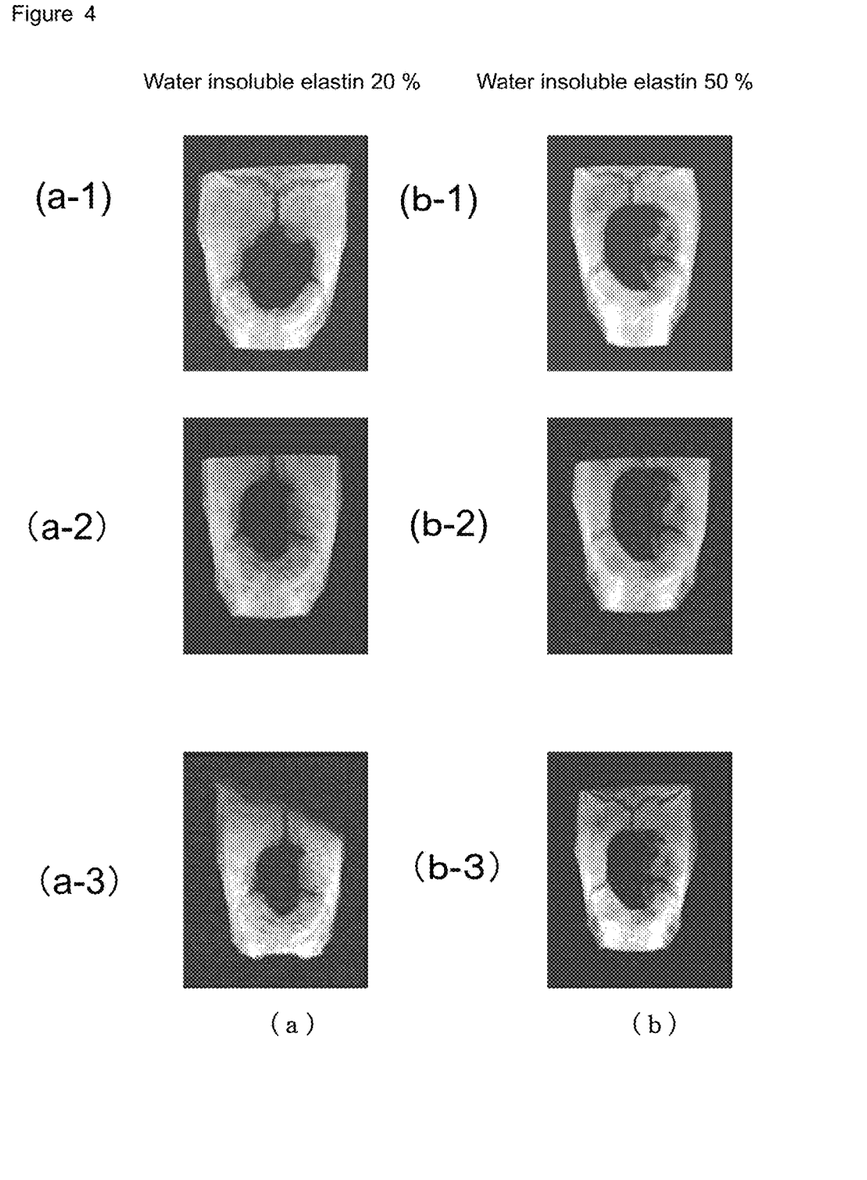
Figure 5:
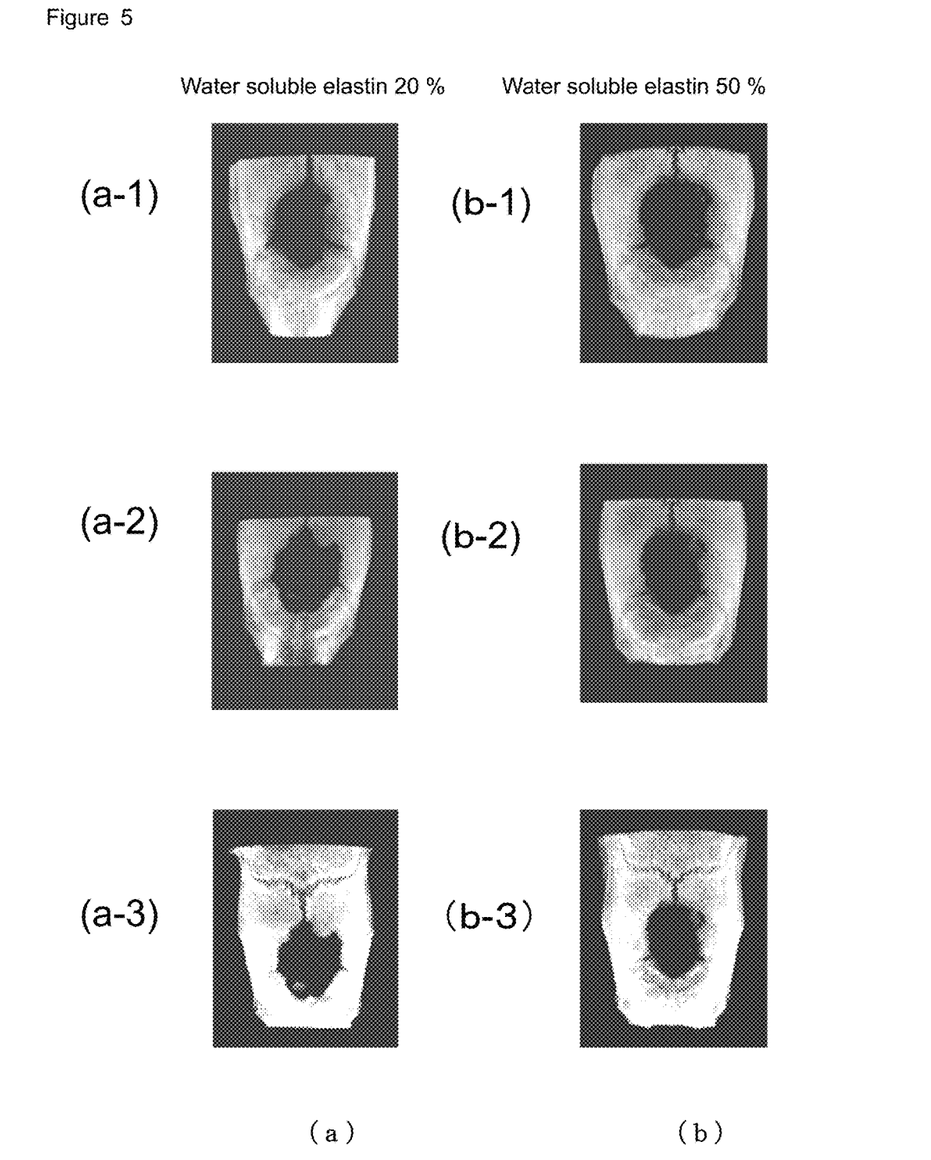
Figure 6:
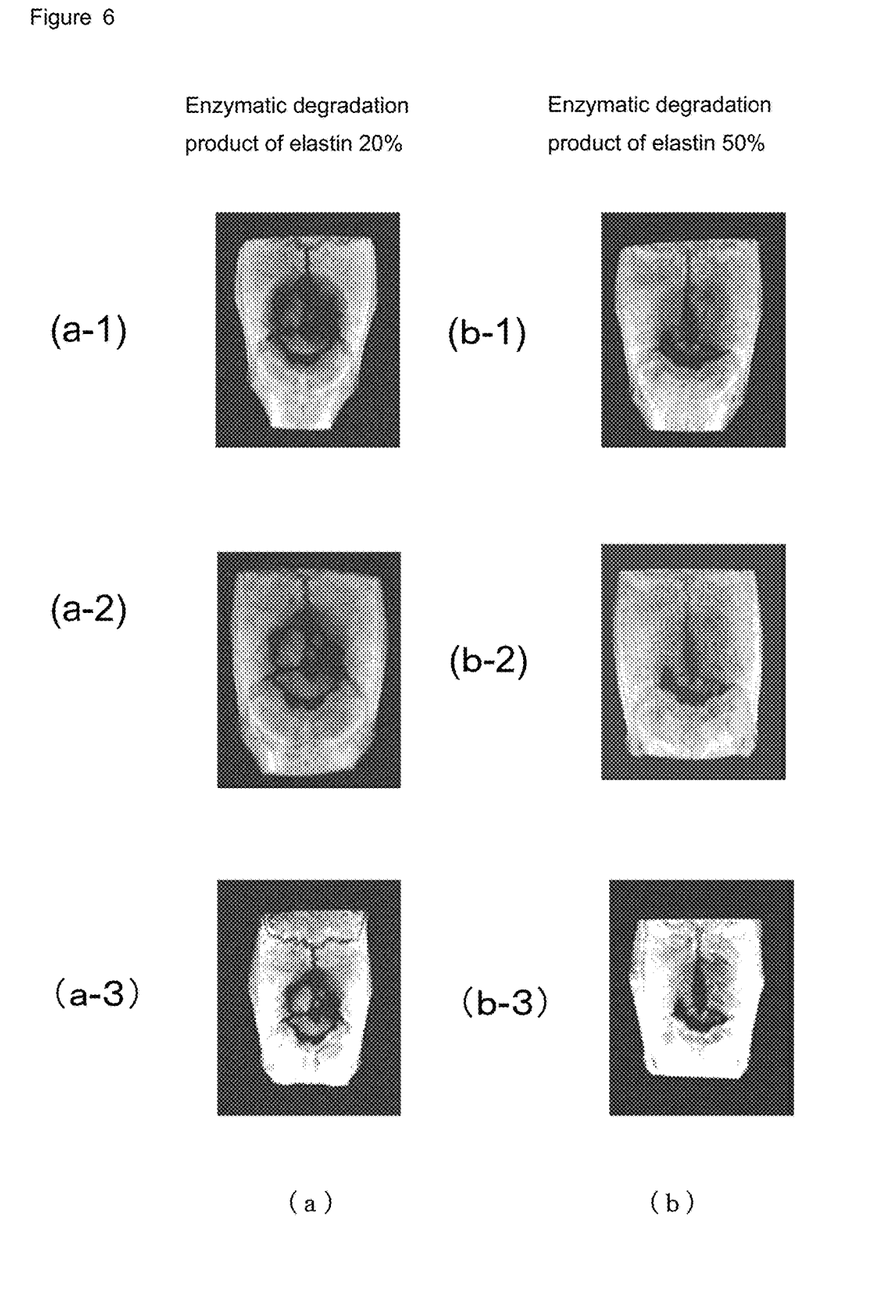

The salmon heart was treated with Protease Amano P6 (Amano Enzyme Inc.), and only the bulbus arteriosus was recovered as a residue from the salmon heart. The recovered bulbus arteriosus was treated with a 0.06% (w/w) sodium hydroxide solution at 40° C. overnight, neutralized with hydrochloric acid, and heated for 15 minutes after reaching 80° C. by a hot water bath to further dissolve and remove contaminating proteins etc. in the bulbus arteriosus to provide water-insoluble elastin. Oxalic acid or acetic acid was added to the water-insoluble elastin, which was then subjected to filter filtration to remove a solid content; after removing acid by ultrafilter treatment (5,000 Da), the resultant was freeze-dried to provide water-soluble elastin. On the other hand, the water-insoluble elastin was treated for 4 hours by adding Alcalase 2.4 L FG (Novozymes A/S), treated for 4 hours by adding Protex 6 L (Genencor Kyowa Co. Ltd.), subjected to filter filtration by adding activated carbon after deactivation by heating, and freeze-dried to provide an enzymatic degradation product of elastin. As a result of analysis by gel filtration chromatography, the molecular weight of the water-soluble elastin was found to be 9,100 to 97,500 Da, and the molecular weight of the enzymatic degradation product of elastin was found to be 350 to 3,600 Da. The water-insoluble elastin was not measured for molecular weight distribution because of its insolubility. Chromatograms of gel filtration chromatography are shown in FIGS. 1 to 2. The analysis conditions for GPC included a column: TSK-Gel G3000 PW×1, solvent: 0.1% trifluoroacetic acid-containing 45% acetonitrile, and standard: glutathione (307 Da), bradykinin (1,060 Da), α-melanocyte stimulation hormone (1,665 Da), oxidized insulin B chain (3,496 Da), aprotinin (6,512 Da), cytochrome C (12,400 Da), carbonic anhydrase (29,000 Da), albumin (66,000 Da), or alcohol dehydrogenase (150,000 Da).

(Preparation of DNA/Protamine/Elastin Complex)

An appropriate amount of deionized water was added to a powdered DNA/protamine complex, which was then kneaded in an agate mortar to prepare a DNA/protamine complex paste. The enzymatic degradation product of elastin, the water-soluble elastin, and the water-insoluble elastin were each added to the paste in small portions while kneading in an agate mortar to 20% (w/w) or 50% (w/w) to prepare a DNA/protamine/elastin complex paste, respectively.

Example 2

(Confirmation of Osteogenesis Ability of DNA/Protamine/Elastin Complex)

(a) Sample

Each DNA/protamine/elastin complex paste obtained in Example 1 was packed in a silicon mold having an internal diameter of 8 mm and a thickness of 1.5 mm to prepare a DNA/protamine/elastin complex disk. A loss of 5 mm in diameter was produced in a skull bone site in each of 10-week old SP rats (specific pathogen free rats, male) using a trephine bar, and a disk-shaped complex was embedded therein. After embedding, the periosteum and the epithelium were sutured.

(b) Evaluation of New Bone Formation:

The tomographic image of the area of skull bone loss was taken in the same individual on the 1, 2, and 3 months after embedding using an X-ray CT scanner (ScanXmate-RB090SS150, from Comscantecno Co., Ltd.) to confirm the presence of the progress of the process of bone formation and to compare the amount of bone formation. A blank as a control group and a 300-bp DNA/protamine complex alone group were similarly evaluated. After 3 months, each embedded sample was also taken out from the surrounding tissue, and the sample was fixed, demineralized, and subjected to HE (hematoxylin-eosin) staining by conventional methods to observe the tissue.

(c) Results and Discussion

The results obtained are shown in FIGS. 3 to 6. FIG. 3(a) shows the state of the μCT images (1 to 3 months after embedding), when no material was embedded in the bone defect part and the part was sutured, FIG. 3(b) shows the state of the μCT images of a DNA/protamine complex embedded part (1 to 3 months after embedding), when the DNA/protamine complex alone was embedded, respectively. The state of the μCT images of DNA/protamine complex-embedded areas (1 to 3 months after embedding) is shown, when 20% (w/w) of water-insoluble elastin was added in FIG. 4(a), and when 50% (w/w) water-insoluble elastin was added. in FIG. 4(b), respectively. The state of the μCT images of DNA/protamine complex-embedded areas (1 to 3 months after embedding) is shown, when 20% (w/w) of water-soluble elastin was added in FIG. 5(a), and when 50% (w/w) water-soluble elastin was added in FIG. 5(b), respectively. The state of the μCT images of DNA/protamine complex-embedded areas (1 to 3 months after embedding) is shown, when 20% (w/w) of an enzymatic degradation product of elastin was added in FIG. 6(a), and when 50% (w/w) of an enzymatic degradation product of elastin was added in FIG. 6(b), respectively. In each of the figures, (a-1) and (b-1) show the states 1 month after embedding; (a-2) and (b-2) show the states 2 month after embedding; and (a-3) and (b-3) show the states 3 months after embedding, respectively.

From the above results, although almost no bone formation was observed after embedding in the blank group, new borne formation was confirmed 3 months after embedding in the DNA/protamine complex alone group. Almost no bone formation was observed even 3 months thereafter in the group in which 20% (w/w) or 50% (w/w) of the water-insoluble elastin was added to the DNA/protamine complex or in which 20% (w/w) or 50% (w/w) of the water-soluble elastin was added thereto. In contrast, in the group in which 20% (w/w) or 50% (w/w) of the enzymatic degradation product of elastin was added to the DNA/protamine complex, new bone formation could be confirmed from 1 month after embedding and the amount of new bone formation increased with time. In these groups, 3 months after embedding, the amount of new bone formation was evidently larger than that in the group in which the DNA/protamine complex was embedded alone, confirming a significant rise in the bone formation rate due to the addition of the enzymatic degradation product of elastin to the DNA/protamine complex. The sample containing 50% (w/w) of the enzymatic degradation product of elastin was superior in bone-forming properties to that containing 20% (w/w) thereof.

Comparative Example 1

Table 1 shows the results of analyzing the molecular weight distribution in the enzymatic degradation product of elastin according to the present invention; α-elastin; and an acid/alkali degradation product of elastin from Elastin Products Company by gel filtration chromatography. The degradation product of elastin according to the present invention was confirmed to have a smaller molecular weight than those of the samples as the comparative examples. It was suggested that a component responsible for activity, strongly promoting bone formation was contained in the low-molecular fraction having a molecular weight of 350 to 990 Da obtained by the enzymatic degradation of the present invention or that a high-molecular fraction having a molecular weight of 3,600 Da or more, not contained in the enzymatic degradation product of the present invention had a possibility of inhibiting bone formation.

TABLE 1

Analysis Results of Gel Filtration Chromatography

| Sample | Molecular Weight Range (Da) | Weight - average molecular weight (Da) |
|---|---|---|
| Enzymatic degradation product of elastin [Comparative Examples] | 352 to 3572 | 1010 |
| α-elastin | 6617 to 46793 | 13855 |
| Acid/alkali degradation product of elastin | 995 to 25531 | 5877 |

Comparative Example 2

Difference in the expression level of a bone formation-related gene was examined in an in vitro evaluation system using osteoblasts with respect to the enzymatic degradation product of elastin according to the present invention; α-elastin; and an acid/alkali degradation product of elastin from Elastin Products Company. The palatal gingiva in 9-week old male rats was collected; the subculture, isolation, and recovery of its cells was performed by an out growth method. The enzymatic degradation product of elastin according to the present invention and the elastin of the Comparative Example were each added in a concentration of 1 μL/mL to the culture solution. RNA was extracted after 48 hours of culture; and the expression level of matrix-metalloprotease-2 (MMP-2) as a gene transforming fibroblasts into osteoblast-like cells was measured using real time PCR. Table 2 shows the results of the relative expression level thereof when cells cultured in only the culture solution were used as a control and the expression level of MMP-2 in the control was set to 1. The enzymatic degradation product of elastin according to the present invention was confirmed to increase the expression level of MMP-2 gene by a factor of 5.7, and the elastin of the Comparative Example was confirmed to produce no change in the expression level of the gene. Thus, the enzymatic degradation product of elastin according to the present invention was shown to specifically increase the expression level of the bone formation-related gene.

TABLE 2

Results of MMP-2 gene expression amount

| Sample | Relative expression amount of MMP-2* |
|---|---|
| Enzymatic degradation product of elastin [Comparative Examples] | 5.65 |
| Non (Control) | 1.00 |
| α-elastin | 0.67 |
| Acid/alkali degradation product of elastin | 0.85 |

*Relative expression amount when the MMP-2 expression amount of the control is set as 1.00.

The invention claimed is:
1. A medical or dental material for osteogenesis, comprising a DNA/protamine/elastin complex, as an active ingredient for bone formation, comprising:
 (1) DNA;
 (2) at least one protamine compound selected from the group consisting of protamine, a protamine derivative, and a prolamine hydrolysate; and

(3) an enzymatic degradation product of elastin having a molecular weight ranging from 350 to 3,600 Da; wherein the DNA and the at least one protamine compound form a DNA/protamine complex and the enzymatic degradation product of elastin is incorporated into the DNA/protamine complex to form the DNA/protamine/elastin complex; wherein the ratio of the DNA and the at least one protamine compound is from about 1:9 to about 9:1 by weight; and wherein about 1 to about 75 parts by weight for the enzymatic degradation product of elastin is blended with about 100 parts by weight of the DNA/protamine complex.

2. The medical or dental material according to claim 1, wherein a further medicinal ingredient is trapped by intercalation and/or groove binding within the DNA.

3. The medical or dental material according to claim 1, wherein a bone formation factor or a growth factor is carried.

4. The medical or dental material according to claim 1, wherein the material comprises calcium phosphate.

5. The medical or dental material according to claim 1, wherein the complex has formability enabling injection of the material to an area of bone loss or an area of alveolar bone loss.

6. The medical or dental material according to claim 1, wherein the ratio of the DNA and the at least one protamine compound is from about 1:1 to about 1:1.5 by weight.

7. The medical or dental material according to claim 1, wherein about 20 to about 50 parts by weight of the enzymatic degradation product of elastin is blended with about 100 parts by weight of the DNA/protamine complex.

8. The medical or dental material according to claim 1, wherein about 50 parts by weight of the enzymatic degradation product of elastin is blended with about 100 parts by weight of the DNA/protamine complex.

9. The medical or dental material according to claim 1, wherein the elastin is a cardiac bulbus arteriosus elastin of a fish, a cow, or a pig.

* * * * *